United States Patent [19]

Jäckle

[11] Patent Number: 4,457,163

[45] Date of Patent: Jul. 3, 1984

[54] METHOD AND APPARATUS FOR LOCATING PIPELINE DAMAGE

[76] Inventor: Eugen Jäckle, Galenweg 16, D-8601 Baunach, Fed. Rep. of Germany

[21] Appl. No.: 363,879

[22] Filed: Mar. 31, 1982

[30] Foreign Application Priority Data

Mar. 31, 1981 [DE] Fed. Rep. of Germany ....... 3112829

[51] Int. Cl.³ .............................................. G01M 3/24
[52] U.S. Cl. ................................................. 73/40.5 A
[58] Field of Search ...................... 73/40.5 A, 647, 592

[56] References Cited

U.S. PATENT DOCUMENTS 3,200,899  8/1965  Krauss .................................... 73/647
3,626,750  12/1971  Talmon ............................. 73/40.5 A

FOREIGN PATENT DOCUMENTS 593045  2/1978  U.S.S.R. .......................... 73/40.5 A

OTHER PUBLICATIONS

Sabo, "Detect buried steam leak with acoustics", 7/1976.
Hewlett-Packard Journal, 5/1967.

Primary Examiner—S. Clement Swisher
Assistant Examiner—Hezron Williams
Attorney, Agent, or Firm—Boniard I. Brown

[57] ABSTRACT

Apparatus and method are provided for the location of pipeline damage and medium leak therefrom by acoustical monitoring of the soil about a pipe and recording emission noise by microphone and an amplifier which controls a peak noise indicator. Each measurement point detected by the amplifier is applied to a digital memory to display a histogram showing noise distribution along the pipe. The main frequency of the loudest measurement point is determined, and an octave filter is utilized to determine the frequency characterizing medium leakage to precisely locate the pipeline damage. Bar diagrams may be provided on a viewplate by bands of parallel arrays of light emitting diodes to display noise distribution along the pipeline. A frequency analyzer may transmit from the amplifier to the memory the peak frequency value of each observed frequency band to enable frequency analysis of the loudest measurement point. The apparatus may have a case with a lid defining openings sized for viewing the bar diagrams.

2 Claims, 5 Drawing Figures

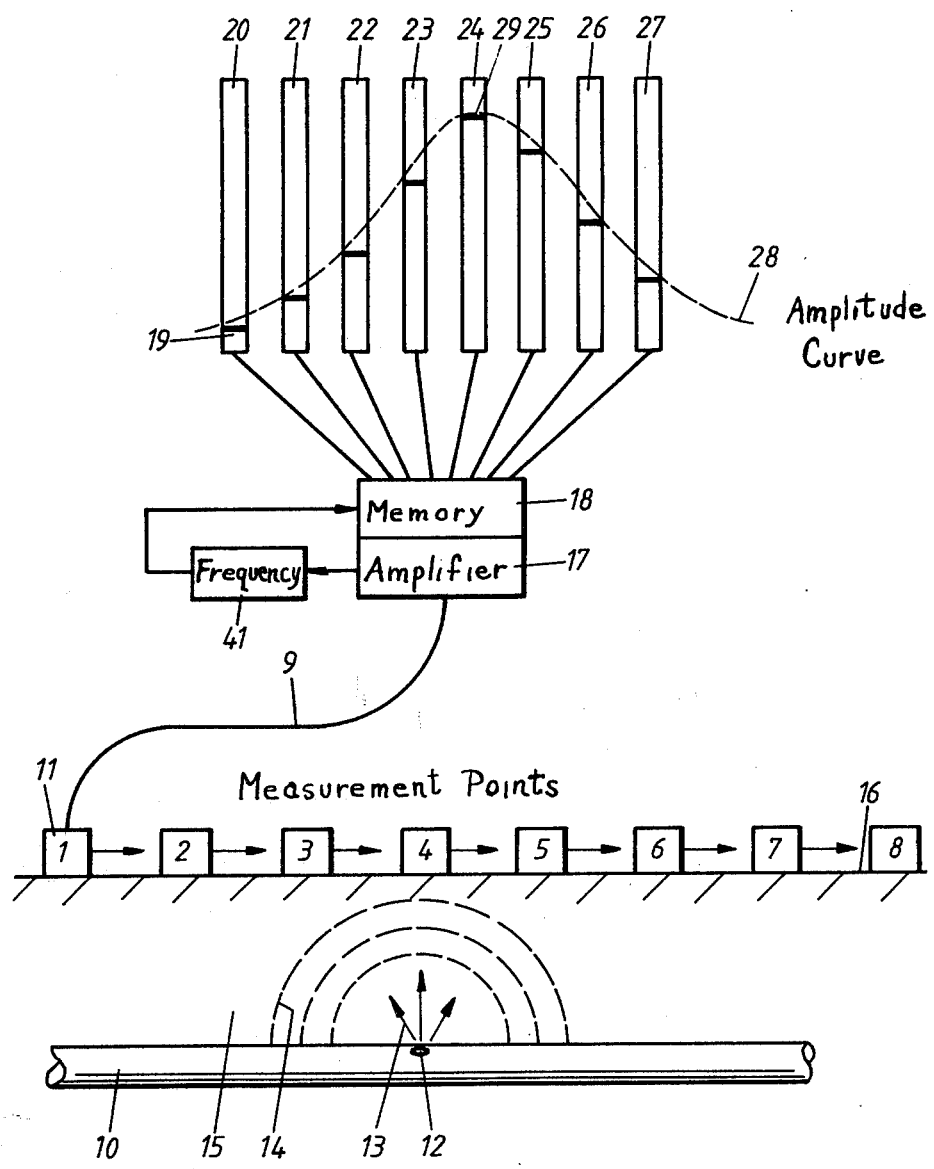

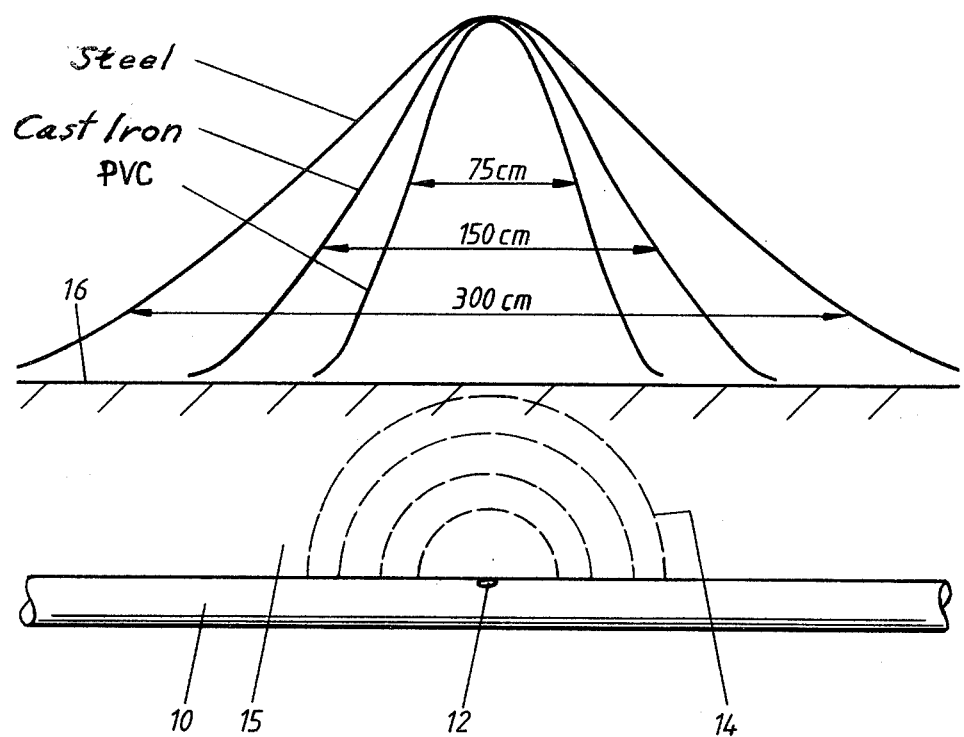

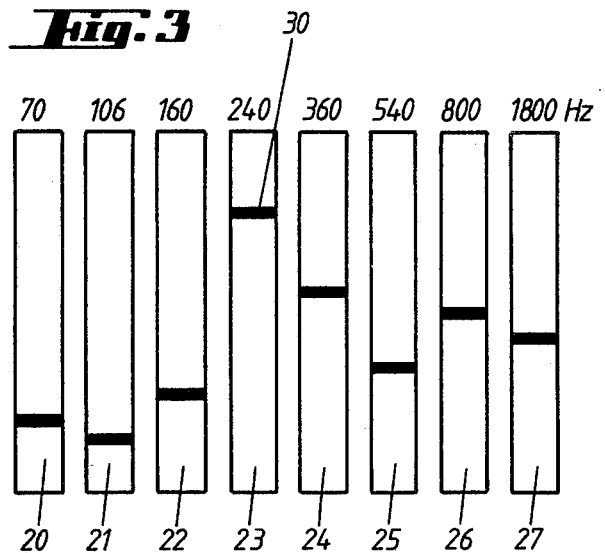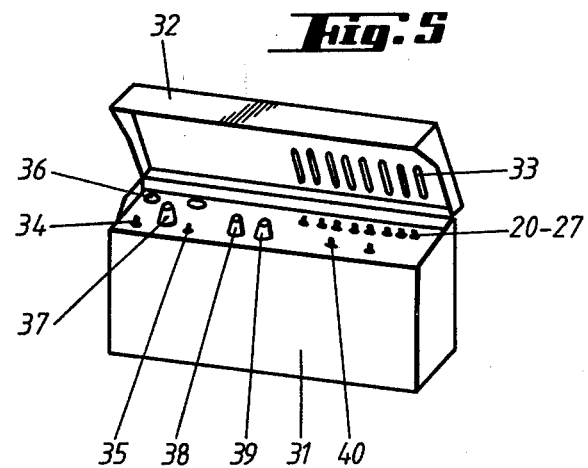

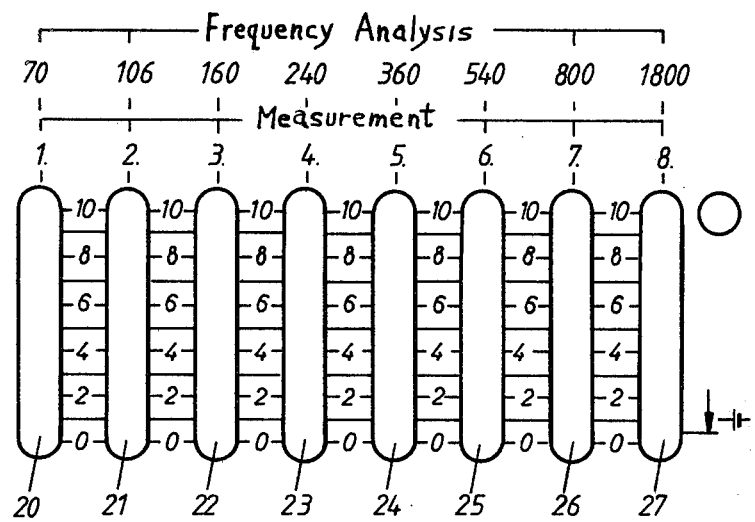

METHOD AND APPARATUS FOR LOCATING PIPELINE DAMAGE

BACKGROUND AND SUMMARY OF THE INVENTION

The object of the invention is a method and an instrument for locating pipeline damage by acoustically monitoring the soil surrounding the defective pipe and detecting the emission noise by means of microphones connected to the input of an amplifier that controls a noise peak display.

Electronic pipeline damage detectors operating on the "listening principle" have been successfully used for years. Yet, there are recurrent cases where pipe breaks cannot be found in spite of the greatest instrument amplification (1.1 million). As a consequence, one must put up with unwarranted digging, because the instrument gives a clear indication that a break may be assumed at some given place or other. The reason for these phenomena lies in the physics of a pipe break. The medium water is known to flow out of the pipe under pressure and against the surrounding soil.

At the emission point of this stream of water, solid-borne sound is generated, which spreads spherically. It travels to the surface for one and, for another, induces the pipeline to oscillate via the soil. Depending on the impact pressure, the resonance characteristics of the pipe, and the solid-borne sound attenuation of the soil, different frequencies and intensities may occur at the surface. Apart from that, reflection occurs in the vicinity of foundation walls, gully holes, etc., which are superimposed on the actual leakage noise.

The sound conductivity of steel, cast iron, and plastic pipes varies significantly. The sound conductivity of plastic pipes, be they PVC, PE, or AC, is very low. In measurements, it may be neglected. Because of this situation, the interval between measurement points must be handled differently in the microphone listening method. In accordance with FIG. 1, a measurement point interval of about 3 m is sufficient for steel pipe. For cast iron pipes 1.50 m are required, and for plastic pipe 0.75 m. When the intervals chosen to acoustically monitor a pipeline are too large, there is a risk that a leak will be missed. This problem is to be expected, especially in the case of a nonmetallic pipe with a punctual propagation zone of the solid-borne sound.

If a noise is detected above the line, this need not necessarily be the expected leakage noise. Solid-borne sound waves are common in the soil and can easily simulate a leak. Momentary events, such as knocking, hammering, rattling, etc. are recognized as interference by the ear as well as the instrument and do not cause any special problem. But the situation is different with continuous vibrations that take the form of continuous noise. These interference vibrations may originate in transformers, motors, compressors, bearings, etc. Technical equipment and machinery firmly anchored in the foundations of buildings generate a large number of solid-borne oscillations, which are generally very well conducted by the soil. These vibrations, however, generally have entirely different frequencies than those originating from the leak. If the measuring technician is capable of distinguishing frequencies by ear, he is capable of detecting the actual leakage frequency in a whole spectrum of frequencies. The volume indicator of his amplifier is of little help, since it only indicates the loudest frequency, even if this is the interference frequency.

In order to deal with the cited difficulties, a completely new pipeline rupture detector has been developed. Its essential innovations are:
1. memory for measurement values
2. frequency analysis
3. octave filter Pipeline rupture detection is conducted in the form of a series measurement, i.e. the ground microphone is set up at suitable intervals above the pipeline, and the location with the largest solid-borne sound intensity is determined. For this purpose the ground microphone must be repeatedly moved in the area of the leak, in order to find the culmination point, i.e. the location of the highest solid-borne sound intensity. The measurement technician must concentrate on each measurement, i.e. each new setup of the ground microphone, and must adapt himself physically and psychologically to the measurement. This adjustment cannot be expected of a single person indefinitely, because of fatigue, introducing another chance that a signal will be overheard or misinterpreted.

The present invention has made it its task to significantly improve a method for locating pipeline ruptures of the initially cited kind and an instrument operating on that principle. Specifically, location was to be made faster, more accurate, and operationally safer.

In the solution of this problem, the method is characterized in that, in a first process phase, the noise peak of each measurement point, detected by the amplifier, is transmitted to a digital memory for measurement values, which displays a histogram of the noise distribution along the measurement distance above the pipe, and that, in a second process phase, the main and preferred frequency of the loudest measurement point is determined on a broad band and that an octave filter is used to determine the characteristic frequency of the emitted medium from the main and preferred frequency as determined at a broad band, for the purpose of precise location.

The new method utilizing an electronic memory for measurement values eliminates these shortcomings. The instrument has eight such memories, which are successively activated. At measurement point 1, the noise recorded by the ground microphone is also displayed on a linear scale of light emitting diodes.

The scale covers a range from 0 to 10. Only the highese point of a measurement value appears. This LED scale is brightness controlled, so that it can be conveniently read, even in bright daylight. At night the usual illumination of the scale is obviated.

When a measurement value is to be stored, the scale value is transmitted to an electronic memory and can be held there for hours. Then measurement point "2" is monitored, and the solid-borne sound occurring at that point is displayed on the second scale. This value is subsequently also stored. Eight measurement points are thus successively checked, and their measurement values recorded. After activation and display of all eight measurement values, these can all be observed at the same time, and one can easily recognize the measurement point at which the greatest solidborne sound intensity was measured. The line connecting the top scale markings thus provides a volume diagram for the tested distances.

The memory for measurement values is also used to locate the general area of leaks in the water pipe network. To date, the values obtained with a probe at accessible contact points had to be recorded in order to find the loss section between two listening points. Here, one measurement value after another is stored, and in the "poll" mode one then obtains accurate information between which measurement points the loss line lies.

As pointed out above, the place of the greatest volume need not be the leak. For this reason, the noise, resp. frequency spectrum occurring at this point is analyzed, i.e. the individual frequency components are determined. This differentiation of different frequencies, which is not always easy for the human ear, is performed electronically by this instrument. The eight LED scales are each allocated to a certain frequency. The frequency from one step to the next is always 1.5 octaves and covers the frequency range from 70 cps to 1,800 cps which is relevant to leak detection.

These frequencies are specifically:

70—106—160—240—360—540—800—1,800 cps.

For frequency analysis, the geophone is set up at the loudest measurement point, and broad band amplification is selected to keep signals from exceeding the scale range. The individual scales then indicate the intensity of their associated frequencies. One can thus determine, for example, the main and preferred frequency of leakage noises without involving the human ear. Empirically, frequencies above 600 cps are unusual in leak location and must therefore be regarded as interference frequencies.

Precision location is the next step. In order to allow it to filter out interference frequencies, the instrument is switched from its previous broad band mode to a filter amplifier mode. Eight highly selective electronic filters, in octave spacing, are available for this purpose. The leak frequency, determined by means of frequency analysis, is selected in one of the eight filters, so that the amplifier now singles out this frequency for amplification, suppressing other, interference, frequencies to a large extent. This guarantees that for precision location only the actually interesting frequency is amplified, monitored, and measured. This prevents a wrong filter setting, which is unavoidable without frequency analysis.

The interaction of these three new assemblies, in conjunction with an industry-proven, low noise amplifier, allows faster and more accurate pipe leak location. The burden on the measurement personnel is also reduced, so that greater efficiency may be expected in this respect as well.

The object of the present invention arises not only out of the object of the individual patent claims, but also out of the mutual combination of the individual patent claims.

All of the statements and characteristics revealed in the documentation, especially the spatial configuration represented in the drawings, are claimed as being essential to the invention, insofar as they are new with respect to the state of the art, either singly or in combination.

The invention is explained in greater detail below, using drawings that illustrate only one possible implementation. The drawings and their description reveal other features and advantages of the invention, which are essential to the invention.

BRIEF DESCRIPTION OF THE DRAWINGS

FIG. 1 shows the method according to the invention in schematic with parts of the instrument;

FIG. 2 shows the noise curve (amplitude as function of the distance from the point of emission at the pipe) above a defect in the pipe;

FIG. 3 shows the frequency display of frequency analysis with the aid of the light emitting diode displays;

FIG. 4 shows the bar diagram display on the instrument;

FIG. 5 is a perspective front view of the instrument with half-opened lid.

DESCRIPTION OF THE PREFERRED EMBODIMENT

FIG. 1 shows a defective pipe 10 in schematic, located in soil 15, from which water, for example, emerges in the direction of the arrow 13 at the emission point 12, causing a noise in the form of a spherical wave 14, which propagates spherically in the soil 15 and reaches the surface 16 of the soil 15, among other places. At the surface and along the path of the pipe, a measurement microphone 11 is set up at measurement point 1, which is connected to an analog amplifier 17 via a measuring cable 9. The amplifier 17 operates as analog peak amplifier in the first part of the process, where the noise peak detected by the measurement microphone 11 is applied to a digital memory 18, which places the detected noise peak onto the memory display 19 in the bar diagram display 20.

The bar diagram 20 may consist either of a fluorescent display or a line of light emitting diodes, where only the peak value is displayed on the light emitting diode display.

The measurement microphone 11 is now shifted to the place of the measurement point 2, the noise is again detected via the amplifier 17, and the noise peak is applied to the memory 18, which displays it on the bar diagram 21. One proceeds in the same manner with measurement point 3 and the bar diagram 22, likewise with measurement point 4, which displays its noise peak on bar diagram 23; the measurement points 5-8 are associated with bar diagrams 24-27.

If one connects all the peaks of the bar diagrams, one obtains an amplitude curve 28, where the bar diagram 24 displays the noise peak 29. One now knows that the defective place must be sought in the vicinity of measurement point 4-5.

The distance of measurement points 1-8 is shown in the diagram of FIG. 2 which shows that, with a PVC pipe, the measurement point interval must not be greater than 75 cm, while the distance between measurement points may be up to 300 cm with a steel pipe.

The measurement microphone 11 can then be successively placed on the ground at several closer points at the measurement points 4-5, by which means one can produce additional amplitude curves on the bar diagram 20-27.

In this manner one can very quickly and very accurately localize the defect, this is the emission point 12 in the defective pipe 10.

For frequency analysis, the amplifier 17 is switched over, and the defect noise obtained at the loudest measurement point is applied by the amplifier to a frequency analyzer 41, which produces a frequency histogram in the memory 18 and on the bar diagrams 20-27—as illustrated in FIG. 3. Here one can see that in the localized defect noise a frequency of 250 cps predominates.

One is therefore dealing with a frequency peak 30 in the area of 240 cps.

FIG. 4 shows an example of the face labeling of the bar diagram display, revealing a graduated scale from 0-10, with eight measurements being conducted in accordance with FIG. 1 and the corresponding description. At the point of the loudest defect noise one switches to frequency analysis, and the upper labels which refer to the frequency band then apply so that the bar diagrams provided on the instrument can be used for determining the noise peak as well as the frequency distribution in the defect noise. This is, therefore, a pure histogram display.

FIG. 5 shows the example of an implementation of such an instrument, housed in a case 31 with a lid 32 that is hinged at the top. The lid 32 provides cutouts 33 that are suitable in size and configuration, so that the scale with its bar diagrams 20-27 shown in FIG. 4 is visible from the outside when the lid 32 is closed. The light emitting diode display is brightness controlled in relationship to daylight, so that safe display and readout are possible even in bright light.

A power switch 34 for selecting the AC voltage is provided, as well as a battery switch 35, with which the unit can be operated independently of the power grid. There is also a headphone connection 36 to provide a headphone listening mode, apart from the loudspeaker listening mode. An octave filter 37 can be activated for precision frequency analysis. The scale adjustment is made with the amplification control 38. The control 39 adjusts the headphone volume, while the mode switch 40 switches from frequency analysis to peak noise measurement and vice versa.

The entire instrument is very small and handy and represents significant labor savings in the location of pipeline defects, as well as a significant improvement in operational safety.

The inventor claims:

1. A method of pipeline damage and fluid leak location by acoustical monitoring of the soil surrounding a defective pipe and recording emission noise by at least one microphone means connected with the input of an amplifier means, said method comprising the steps of:

applying noise signals received by the microphone means over a broad acoustic frequency band at a plurality of regularly spaced intervals through the amplifier to a digital signal memory such that a histogram indicating the noise distribution along the length of the pipe at each of the intervals may be retrieved and displayed, comparing the frequency content of at least one of the highest peak noise intervals on the histogram with a preferred frequency indicative of the fluid leak such that the interval containing the highest intensity of noise at the preferred frequency may be identified, and as necessary, rerecording the noise signals at closer spaced intervals into the digital signal memory through a relatively narrow bandpass audio filter containing the preferred frequency such that an additional histogram may be displayed at the closer intervals to precisely locate the pipeline damage.

2. Apparatus for pipeline damage and fluid leak location by acoustically monitoring the soil about a defective pipe and recording the emission noise by microphone means connected with the input of an amplifier, said apparatus comprising:

amplifier means to amplify the noise received by the microphone means at each of a plurality of regularly spaced measurement points, a digital signal memory to which said amplified noise from each of the plurality of measurement points is stored such that a histogram indicating the noise distribution along the entire measured length of the pipeline may be displayed simultaneously, and frequency analyzer means comprising a plurality of narrow band audio filters covering a broad audio frequency range which contains a preferred frequency characteristic of the fluid emission, and a plurality of vertical bands of light emitting diodes in side-by-side array to form bar diagrams on a viewplate, one measurement point being associated with each such bar diagram, whereby the noise distribution is displayed along the length of the pipeline.

* * * * *